United States Patent
McFerron

(10) Patent No.: US 9,671,504 B2
(45) Date of Patent: Jun. 6, 2017

(54) SURGICAL PROBE APPARATUS AND SYSTEM

(75) Inventor: Richard McFerron, Columbus, OH (US)

(73) Assignee: Devicor Medical Products, Inc., Sharonville, OH (US)

(*) Notice: Subject to any disclaimer, the term of this patent is extended or adjusted under 35 U.S.C. 154(b) by 765 days.

(21) Appl. No.: 12/491,505

(22) Filed: Jun. 25, 2009

(65) Prior Publication Data
US 2009/0326371 A1    Dec. 31, 2009

Related U.S. Application Data

(60) Provisional application No. 61/075,531, filed on Jun. 25, 2008.

(51) Int. Cl.
*A61B 6/00* (2006.01)
*G01T 1/161* (2006.01)

(52) U.S. Cl.
CPC ............ *G01T 1/161* (2013.01); *A61B 6/4258* (2013.01)

(58) Field of Classification Search
USPC ........................................................ 600/436
See application file for complete search history.

(56) References Cited

U.S. PATENT DOCUMENTS

| | | | |
|---|---|---|---|
| 4,782,840 A | 11/1988 | Martin, Jr. et al. | |
| 4,801,803 A * | 1/1989 | Denen et al. | 250/336.1 |
| 4,889,991 A * | 12/1989 | Ramsey et al. | 250/336.1 |
| 5,441,050 A | 8/1995 | Thurston et al. | |
| 5,495,111 A | 2/1996 | Thurston et al. | |
| 5,732,704 A | 3/1998 | Thurston et al. | |
| 5,744,805 A | 4/1998 | Raylman et al. | |
| 5,932,879 A | 8/1999 | Raylman et al. | |
| 5,937,059 A * | 8/1999 | Kim et al. | 379/386 |
| 6,076,009 A | 6/2000 | Raylman et al. | |
| 6,144,876 A | 11/2000 | Bouton | |

(Continued)

FOREIGN PATENT DOCUMENTS

WO    WO 01/33796 A1    10/2001
WO    WO 2007/131481    * 11/2007

OTHER PUBLICATIONS

Love, Jonathan, "Process Automation Handbook: A Guide to Theory and Practice", 2007.*

(Continued)

*Primary Examiner* — Christopher Cook
(74) *Attorney, Agent, or Firm* — Arent Fox LLP

(57) ABSTRACT

A system for detecting and locating sources of radiation emissions. A hand-held probe includes a detector configured to generate a low-level electrical signal relating to a radiation source proximate the detector, and a probe wireless link configured to transmit a message containing gamma data relating to the low-level electrical signal. An instrumentation console includes a housing, an integral console wireless link within the housing and configured to receive the message transmitted by the probe wireless link, a receiver electrically coupled to the console wireless link to convert the message to corresponding electrical display signals, and a visually perceivable display electrically coupled to the receiver to convert the electrical display signals to a visually perceivable display relating to the amount of radiation detected.

20 Claims, 4 Drawing Sheets

(56) References Cited

U.S. PATENT DOCUMENTS

| | | |
|---|---|---|
| 6,191,422 B1 | 2/2001 | Thurston |
| 6,204,505 B1 | 3/2001 | Call |
| 6,218,669 B1 | 4/2001 | Call |
| 6,222,193 B1 | 4/2001 | Thurston et al. |
| 6,236,880 B1 * | 5/2001 | Raylman et al. ............. 600/436 |
| 6,259,095 B1 | 7/2001 | Bouton et al. |
| 6,272,373 B1 * | 8/2001 | Bouton ......................... 600/436 |
| 6,331,703 B1 * | 12/2001 | Yarnall ................ A61B 6/4057 |
| | | 250/336.1 |
| 6,456,869 B1 | 9/2002 | Raylman et al. |
| 6,771,802 B1 * | 8/2004 | Patt et al. ..................... 382/128 |
| 2002/0019584 A1 * | 2/2002 | Schulze et al. ............... 600/300 |
| 2003/0093129 A1 * | 5/2003 | Nicolelis et al. ............... 607/45 |
| 2003/0139664 A1 | 7/2003 | Hunt et al. |
| 2004/0061059 A1 | 4/2004 | Gobel et al. |
| 2004/0096069 A1 * | 5/2004 | Chien ............................ 381/67 |
| 2004/0242258 A1 * | 12/2004 | Kim ............................. 455/522 |
| 2005/0095611 A1 * | 5/2005 | Chan et al. ....................... 435/6 |
| 2006/0213754 A1 | 9/2006 | Jarrett et al. .................. 200/43.01 |
| 2007/0054245 A1 * | 3/2007 | Greenfield et al. ........... 434/112 |
| 2008/0114852 A1 * | 5/2008 | Claus ..................... H04L 69/40 |
| | | 709/209 |
| 2009/0177082 A1 * | 7/2009 | Baerwolff et al. ............ 600/436 |

OTHER PUBLICATIONS

Philips, "UART to Bluetooth Interfacing", Application Note, Aug. 2004.*
International Search Report, Patent Cooperation Treaty Application No. PCT/US2009/048644, mailed Aug. 17, 2009.

* cited by examiner

SURGICAL PROBE APPARATUS AND SYSTEM

This application claims priority to U.S. provisional patent application No. 61/075,531, filed Jun. 25, 2008, the entire contents of which are hereby incorporated herein by reference thereto.

FIELD

The present invention relates generally to radioimmunoguided surgical system instrumentation, in particular to a wireless probe for use with such a system.

BACKGROUND

Procedures for the treatment of cancer generally have been based upon the natural history of tumor spread, and thence, upon operative and non-operative options available to the physician. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) Typically, large tumor is readily located by the surgeon by visualization at the operating theater, and, in particular, through palpation, i.e., the feel of tumor as opposed to that of normal tissue. To achieve operative success, however, it is necessary for the surgeon to somehow locate "occult" tumor, i.e., tumor which cannot be found by the conventional surgical procedures of sight and feel. Failure to locate and remove such occult tumor generally will result in the continued growth of cancer in the patient, a condition often referred to as "recurrent" cancer.

A much improved method for locating, differentiating, and removing neoplasms uses a radiolabeled antibody injected into the patient. Once injected, such antibodies are known to accumulate in neoplastic tissues at a higher concentration than in normal tissue. A portable radiation detection probe is employed by a surgeon intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure is now known as radioimmunoguided surgery, or RIGS® (RIGS being a registered trademark of Neoprobe Corporation of Dublin, Ohio).

Similarly, Intraoperative Lymphatic Mapping (ILM) may be utilized to study the effect of neoplastic tissue on a patient's lymphatic system. The lymphatic system provides a vital function in fighting disease; however, this intricate network also creates an ideal pathway for cancer cells to travel and spread. For example, certain solid-tumor cancers such as breast, melanoma, lung, colorectal and head-and-neck cancer frequently spread via the lymphatic system.

The spread of cancer to the patient's lymph nodes is typically determined by examination of the nodes along the likely drainage path by pathology to determine if tumor cells are present. It is not uncommon for a surgeon to remove most of the lymph nodes in the area surrounding a solid tumor. This radical and often unnecessary procedure causes a large number of patients to experience significant complications following surgery.

ILM overcomes many of these drawbacks. In an ILM procedure, a radioactive tracing agent is injected at the site of the primary tumor. Following injection, the tracing agent follows the likely drainage path of the tumor to the initial lymph node or nodes that the tumor may be draining to, referred to as the "sentinel node(s)." A gamma radiation detection device is used to detect the tracing agent. Since the lymph nodes are connected, oncologists believe that if the sentinel nodes show no sign of malignancy, then the downstream nodes in the pathway are likely to be clear of disease, as well. As such, the removal of other nearby lymph nodes would be deemed clinically unnecessary. Therefore, the ability to rapidly locate and biopsy sentinel nodes provides vital information to the physician in determining if the cancer has spread or if it is localized to the site of the primary tumor.

Surgical radiation detection instrumentation is comprised generally of a hand-held probe which is in electrical communication with a control console via a flexible cable. This control console is typically located within the operating room facility but out of the sterile field, while the hand-held probe and forward portions of its associated cable are located within that field. The hand-held radiation detecting probe is relatively small and performs in conjunction with a detector such as a cadmium zinc telluride (CZT) crystal. Details of such instrumentation may be found in commonly owned U.S. Pat. No. 4,782,840, the disclosure of which is expressly incorporated herein by reference.

A drawback of current surgical radiation detection instrumentation is the flexible cable extending between the probe and the control console. If the cable is too short it tends to limit the user's flexibility in positioning the probe. Conversely, if the cable is too long it may become entangled with other instrumentation and equipment. Furthermore, a cable that is not adequately or appropriately sterilized or draped is a potential source of contamination of the operative field.

SUMMARY

A system for detecting and locating sources of radiation emission is disclosed according to an embodiment of the present invention. The system comprises an instrumentation console and a handheld probe that are in wireless communication with each other. The probe is used intraoperatively in order to detect sites of radioactivity. The instrumentation console provides an operator of the probe with an indication of radioactivity, aiding to locate occult tissue.

An object of the present invention is a system for detecting and locating sources of radiation emissions. A hand-held probe includes a detector configured to generate a low-level electrical signal relating to a radiation source proximate the detector, and a probe wireless link configured to transmit a message containing gamma data relating to the low-level electrical signal. An instrumentation console includes a housing, a console wireless link within the housing and configured to receive the message transmitted by the probe wireless link, a receiver electrically coupled to the console wireless link to convert the message to corresponding electrical display signals, and a visually perceivable display electrically coupled to the receiver to convert the electrical display signals to a visually perceivable display relating to the amount of radiation detected.

Another object of the present invention is a method for detecting and locating sources of radiation emissions. The method comprises the steps of providing a hand-held probe having a detector, and further including a probe wireless link, and providing an instrumentation console having a housing, a console wireless link within the housing and configured to receive data transmitted by the probe wireless link, a receiver electrically coupled to the console wireless link, and a visually perceivable display electrically coupled to the receiver. The probe is placed proximate a radiation source such that gamma radiation from the radiation source impinges upon the detector. The detector generates a low-level electrical signal. The probe wireless link generates a message containing gamma data relating to the low-level electrical signal and wirelessly transmits the message to the instrumentation console. The receiver converts the message to corresponding electrical display signals, and the display receives and converts the electrical display signals to a visually perceivable display relating to the amount of radiation detected.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

Figure 1:
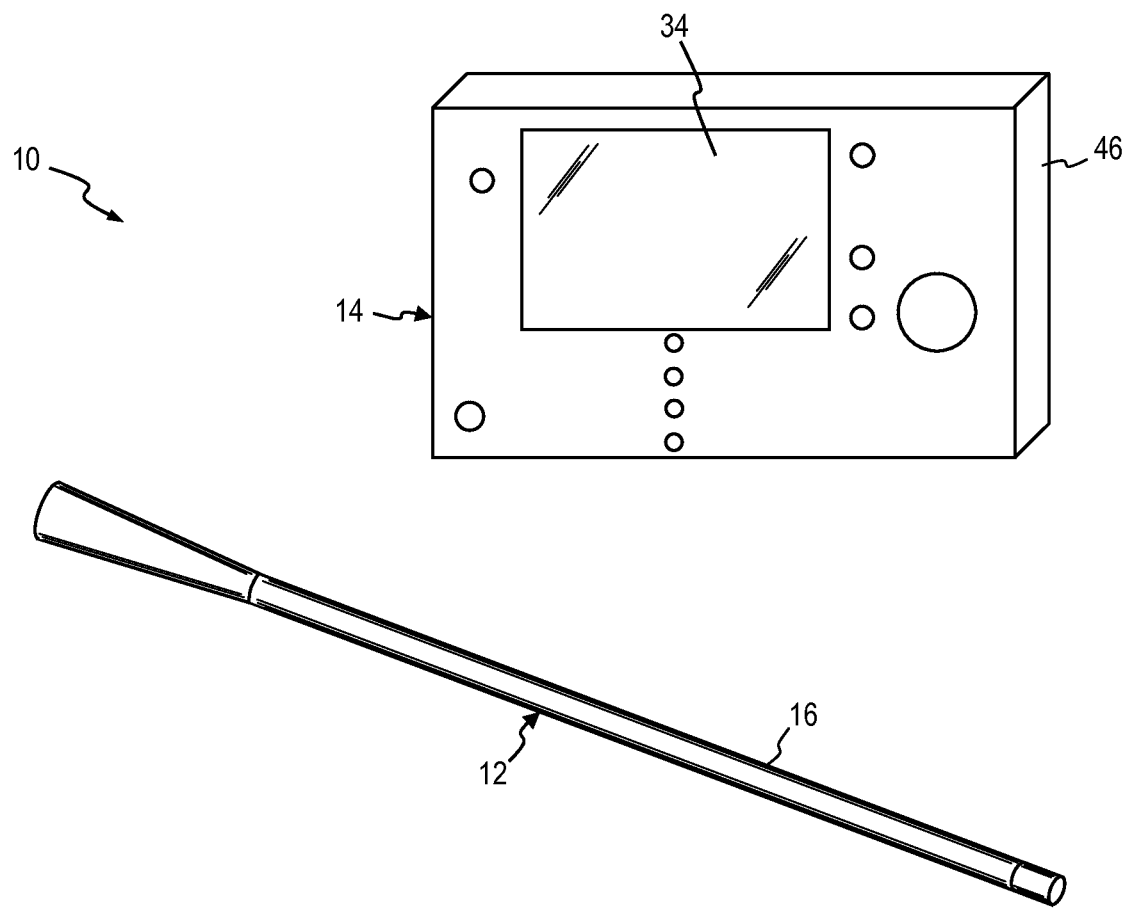
FIG. 1 shows a system for detecting and locating sources of radiation emission comprising a probe and an associated instrumentation console according to an embodiment of the present invention.

The general arrangement of a system 10 for detecting and locating sources of radiation emission is shown in FIG. 1 according to an embodiment of the present invention. System 10 comprises a probe 12 that is in wireless communication with an associated instrumentation console 14. Further details of each are provided below.

A. Probe

Figure 2:
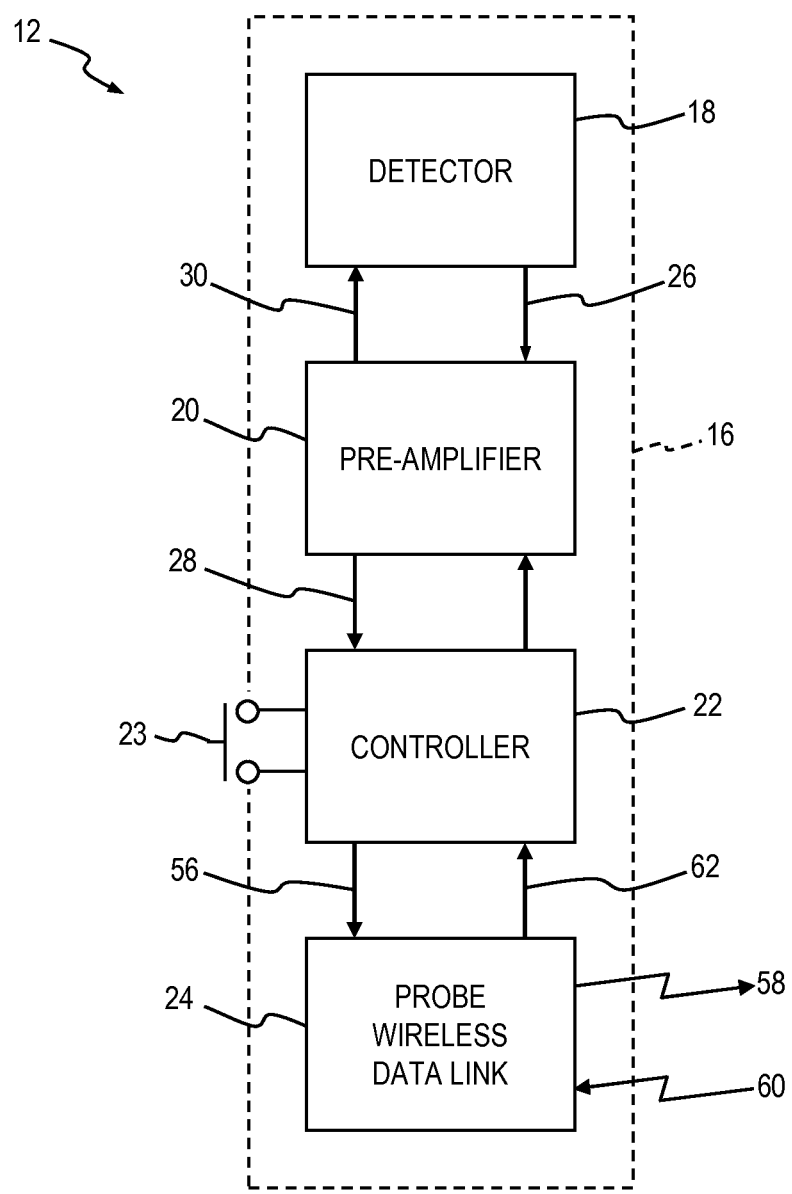
FIG. 2 is a block diagram of the probe of FIG. 1.

With reference to FIGS. 1 and 2, probe 12 includes a housing 16 containing in pertinent part a detector 18, a preamplifier 20, a controller 22 and a probe wireless data link 24. Probe 12 is powered by a not-shown power source, such as a disposable or rechargeable battery.

Detector 18 generates a low-level electrical signal 26 corresponding to the gamma radiation count of tissue proximate the detector. Detector 18 may be made from cadmium zinc telluride or any other semiconductor material suitable for detecting photon radiation. More broadly, detector 18 may be made from any suitable type of crystal that is responsive to gamma radiation emitted by radiolabeled antibodies. For example, detector 18 may comprise cadmium-telluride crystals with or without an alloy, for example, with zinc. Such alloys for the present description may generally and interchangeably be referred to as "Cadmium-telluride," "CdTe" and "CZT." Details of exemplary CZT crystals may be found in commonly assigned U.S. Pat. Nos. 6,218,669, 6,191,422, 5,495,111 and 5,441,050, the entire contents thereof being incorporated herein by reference thereto.

Alternatively, detector 18 may be a scintillating device. The scintillating device may be any type of particle or radiation detector now known or later developed for detecting and counting scintillations produced by ionizing radiation including, but not limited to, cesium iodide. For example, detector 18 configured as a scintillating device may operate through emission of light flashes that are detected by a photosensitive device, such as a photomultiplier or a silicon PIN diode.

Preamplifier 20 receives and amplifies the low-level electrical signal 26 generated by detector 18 to a corresponding output electrical signal 28 of greater magnitude (i.e., voltage and current). Preamplifier 18 may also supply an electrical bias voltage 30 to detector 18 to effect charge migration in the detector when it is exposed to gamma radiation. Details of exemplary preamplifiers may be found in commonly assigned U.S. Pat. Nos. 6,222,193 and 6,204,505, the entire contents thereof being incorporated herein by reference.

Controller 22 receives the output electrical signal 28 from preamplifier 20 and analyzes the output electrical signal to derive gamma data corresponding to the amount of gamma energy detected by detector 18. In some embodiments the gamma data may be in the form of "counts" relating to the number of detected photon radiation impingements. Further details may be found in commonly assigned U.S. Pat. No. 4,889,991, the entire contents thereof being incorporated herein by reference thereto. Controller 22 may also be configured with a control switch 23 to allow a user of probe 12 to set predetermined operating parameters of the probe including, without limitation, a real-time radiation target count and a time-interval accumulated count, and calibration/test. Parameters may be selected by actuating control switch 23 for a predetermined period of time, or by actuating the control switch a predetermined number of times within a predetermined period of time.

Controller 22 may be a digital microprocessor-based control unit configured to operate according to a predetermined control logic to provide control signals for controlling the operation of probe 12. Alternatively, controller 22 may comprise other types of digital-based architectures utilizing, for example, a computer, microcontroller, programmable logic device and the like. The control logic of controller 22 may be defined by a set of predetermined instructions, such as a computer program or "fuzzy logic." Controller 22 may also comprise analog circuitry in whole or in part.

Probe wireless data link 24 (hereinafter termed "probe link 24") is configured for operation in conjunction with an associated instrumentation console data link 32 of console 14 to transfer data between the probe and the console. Probe link 24 may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols such as the BLUETOOTH® standard as promulgated by the Bluetooth Special Interest Group, Inc. (SIG) may also be employed. An example embodiment employing a BLUETOOTH protocol is further described below. Alternatively, a proprietary communication protocol may be utilized.

B. Instrumentation Console

Figure 3:
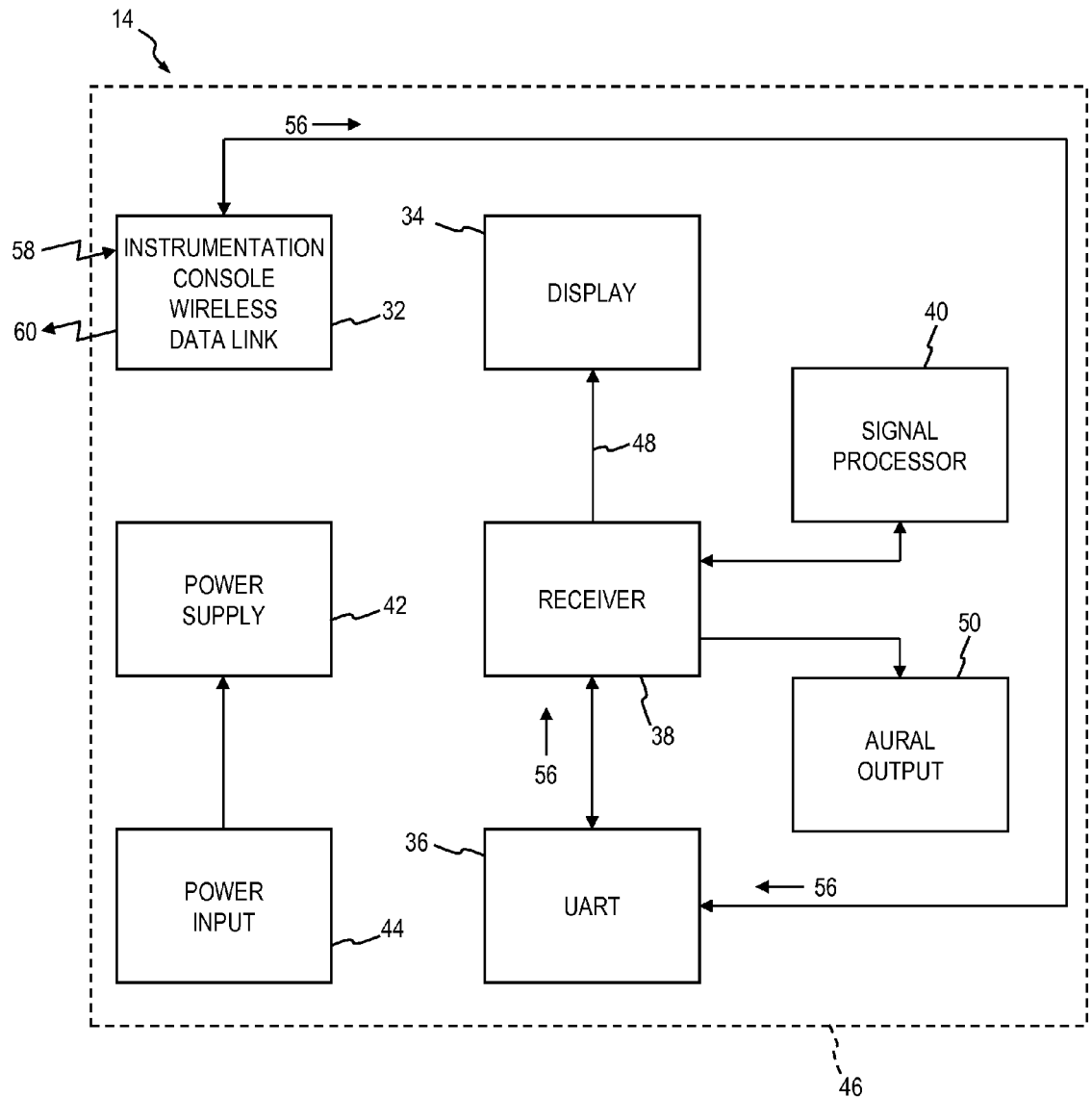
FIG. 3 is a block diagram of the instrumentation console of FIG. 1.
Figure 4:
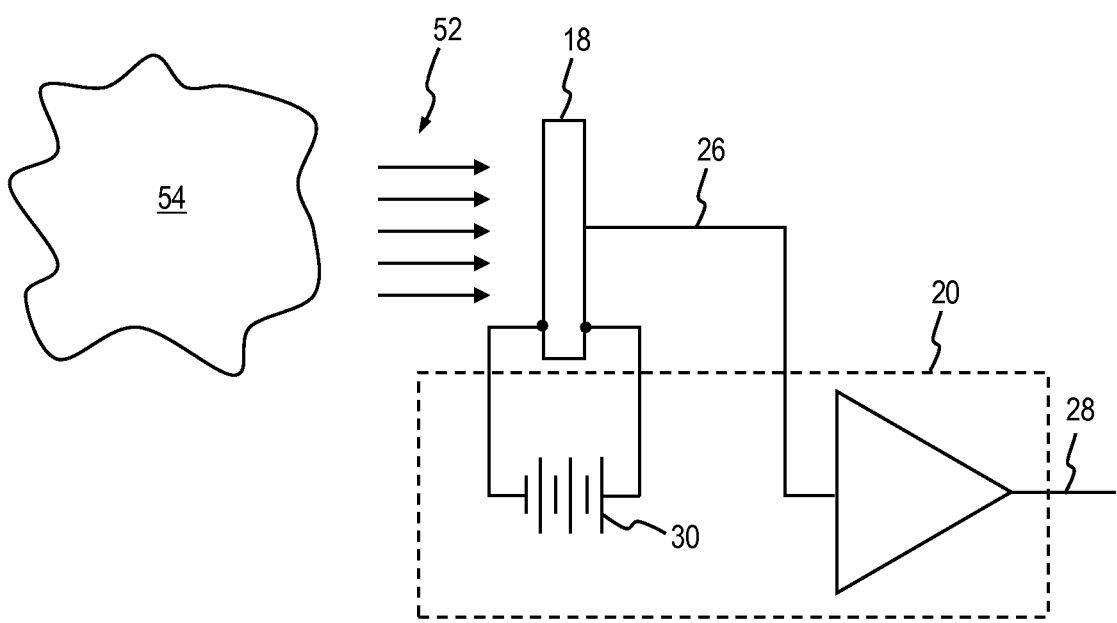
FIG. 4 is a partial schematic diagram of the probe of FIG. 1.

With reference to FIGS. 1 and 3, instrumentation console 14 includes an integral instrumentation console wireless data link 32, a display 34, a universal asynchronous receiver/transmitter (UART) 36, a receiver 38, a signal processor 40, a power supply 42 and a power input 44.

Integral instrumentation console wireless data link 32 (hereinafter termed "console link 32") is integral to, and contained by, a housing 46 of console 14. Console link 32 is configured for operation in conjunction with probe link 24 to transfer data between the probe 12 and instrumentation console 14. Console link 32 may be implemented in any form now known or later invented utilizing, without limitation, radio frequency (RF), visible light, infra-red light, sonic and ultrasonic links and any conventional type of analog or digital modulation including, without limitation, amplitude modulation, frequency modulation, phase shift keying and frequency shift keying. Telecommunication protocols such as the BLUETOOTH® standard as promulgated by the Bluetooth Special Interest Group, Inc. (SIG) may also be employed. A standard Serial Port Protocol (SPP) software package may also be included with console link 32. Alternatively, a proprietary communication protocol may be utilized.

UART 36 is a data communication interface and converter. UART 36 converts data received by console link 32 to a serial data stream and forwards the serial data stream to receiver 38. Likewise, serial data generated by receiver 38 may be forwarded to console link 32 via UART 36 and converted to another data format for transmission to probe 12 via links 24, 32. The serial data stream employed in conjunction with UART 36 may be configured in an Electronic Industries Alliance (EIA) serial data format, such as RS-232, RS-422 and RS-485, or may be a proprietary format.

Receiver 38 receives the serial data stream from UART 36 and converts the serial data stream to electrical display signals 48 having predetermined voltage, current and frequency values corresponding to the content of the data stream. Electrical display signals 48 are coupled to display 34.

Receiver 38 may include a digital microprocessor-based control portion configured to operate according to a predetermined control logic to provide control signals for controlling the operation of instrumentation console 14. Alternatively, receiver 38 may comprise other types of digital-based architectures utilizing, for example, a computer, microcontroller, programmable logic device and the like. The control logic of receiver 38 may be defined by a set of predetermined instructions, such as a computer program or "fuzzy logic." In still other embodiments receiver 38 may be partially or wholly comprised of analog circuitry. Receiver 38 may incorporate, without limitation, any or all of the gamma detection features discussed in commonly assigned U.S. Pat. Nos. 6,272,373, 6,259,095, 6,144,876 and 5,732,704, the entire contents thereof being incorporated herein by reference thereto.

Signal processor 40 may be configured to execute functions relating to analyzing, interpreting and manipulating the serial gamma data. Functions executed by signal processor 40 include, without limitation, filtering, smoothing, noise reduction and thresholding. For example, signal processor 40 may be adjusted by a user of system 10 to set a threshold value of the gamma data such that data having a value below the select threshold is ignored by receiver 38 and not provided to display 34 in the form of electrical display signals 48. A dynamic pitch mode may be selected wherein a baseline value is stored and used as a threshold. Alternatively, a binary pitch mode may be selected wherein a baseline value is stored for comparison, to determine whether a difference in detected radioactivity between a reference (such as background tissue) and a radiation source (such as target tissue) is statistically significant. Signal processor 40 may be configured for use with analog or digital signals, or both.

Display 34 receives electrical display signals 48 and converts the display signals to a visually perceivable indication corresponding to the serial data stream. Display 34 may be any type of visual display now known or later developed including, without limitation, cathode ray tubes, fixed-format liquid crystal displays, plasma displays, active matrix liquid crystal displays and light emitting diode displays. Display 34 may be monochromatic, color or a combination thereof, and may include a backlight.

Instrumentation console 14 may optionally include an aural output subsystem 50 configured to generate an aural signal corresponding to the gamma data in a predetermined manner. For example, the frequency and/or amplitude of the aural signal may be made proportional to a gamma count corresponding to the low-level electrical signal 26 generated by detector 18.

Power supply 42 may be any type of linear or switching-type arrangement for converting mains AC power to one or more predetermined AC and DC voltages and currents required by the components of instrumentation console 14.

Power input 42 may be configured to establish a select AC mains power input, such as 110 or 220 volts AC. Power input module 42 may also include over-voltage protection circuitry, such as transient suppressors, and over-current protection devices, such as fuses and circuit breakers.

C. System Operation

With reference now to FIGS. 1 through 4 together, in operation system 10 detector 18 of probe 12 is electrically biased by bias voltage 30 coupled thereto. Gamma radiation 52 emitted from a source 54 of photon emission radiation impinges upon detector 18, causing the detector to generate a low level electrical signal 26 corresponding to predetermined characteristics of the detected gamma radiation, such as the number of photon impingements or radiation count (hereinafter generally termed "gamma data"). Preamplifier 20 receives and amplifies low-level electrical signal 26 generated by detector 18 to a corresponding output electrical signal 28 of greater amplitude, the output electrical signal likewise corresponding to and representing the gamma data.

Controller 20 receives the gamma data from preamplifier 20 via output electrical signal 28. Controller 20 converts the gamma data to a "message" 56 having a predetermined analog and/or digital format, the message containing information relating the gamma data in said format. Message 56 is periodically transmitted as a component of a probe output signal 58 transmitted by probe link 22 to console link 24. In one embodiment of the present invention message 56 is transmitted about every fifty milliseconds. Message 56 contains a start transmission character, a message type character, the gamma data (two bytes), and a checksum byte (summing all other message bytes). Probe output signal 58 may also include error correction and automatic re-transmission capability to ensure the quality of the data transmission. If BLUETOOTH technology is employed, links 22, 24 may include a frequency hopping technique to avoid interference with other wireless devices.

A self-correction scheme is preferred for probe output signal 58. If probe output signal 58 lacks such self-correction, a stronger message check such as a 16-bit cyclic redundancy check, or CRC may be used. Furthermore, if probe output signal 58 lacks automatic re-transmission, a bidirectional transmitter-receiver handshake scheme may be utilized wherein a console output signal 60 issued wirelessly by console link 32 transmits a confirmation message 62 to probe link 24, the confirmation message being forwarded to controller 22 by the probe link for error-checking comparison with message 56.

Console link 24 forwards message 56 to UART 36, which converts the message to serial format and forwards the message to receiver 38. Receiver 38 validates message 56 using a checksum byte. Once the message is validated, the received gamma data is compared against the last counter value and a difference is calculated. Any 16-bit counter overflow is also taken into account. If the gamma data is in the form of an absolute gamma count a difference calculation is desirable.

The gamma count value is synchronized to a highly accurate internal five millisecond time interval by receiver 38, each time interval being termed a "bin." This synchronization is accomplished so that a stable, accurate gamma data count provided to display 34 in the form of electrical display signals 48, the electrical display signals being converted by the display to a corresponding visually perceivable image representative of the gamma data. Incoming gamma data values are averaged by receiver 38 over the next ten "bins" to derive a smoothed gamma data count. The smoothing operation is preferably configured so that it does not add or remove any gamma counts to the resulting values.

If messages 56 are being lost (i.e., wireless out of range, transmitter turned off, or wireless interference), the gamma data values displayed by display 34 may be set to zero. If no messages are detected for a predetermined minimum period of time, such as for five seconds, receiver 38 may determine that probe output signal 58 has been lost and provides predetermined electrical display signals 48 to display 34 such that the display visually indicates this condition to a user of system 10 in a predetermined manner, such as with a "NO SIGNAL" annunciation.

In some embodiments of the present invention receiver 38 may be coupled to signal processor 40. Signal processor may be configured to execute some or all of the previously noted functions relating to analyzing, interpreting and manipulating the serial gamma data.

In some embodiments of the present invention aural output subsystem 50 may be used in conjunction with display 34, or instead of the display. Aural output subsystem 50 may be configured to generate an aural signal corresponding to the gamma data in a predetermined manner. For example, the frequency and/or amplitude of the aural signal may be proportional to the gamma count.

In previous gamma detection diagnostic systems analog signals from a probe were coupled to a console through a flexible cable. The assignee of this application has previously improved upon the art by developing a wireless link between a probe and a console, but that configuration required an external adapter coupled to a data interface connector of the console. The external adapter is subject to being lost or misplaced, or could be accidentally unplugged, thereby disrupting diagnostic activities that often have been planned well in advance of the procedure. Furthermore, repetitive insertion and removal of the external adapter to the data interface of the console can generate wear of mating connectors on the adapter and console, resulting in intermittent or broken connections. The present invention, which includes a probe 12 having a probe link 22 that communicates with a corresponding console link 24 that is integral to a console 14, represents a significant improvement in the art.

While this invention has been shown and described with respect to a detailed embodiment thereof, it will be understood by those skilled in the art that changes in form and detail thereof may be made without departing from the scope of the claims of the invention.

What is claimed is:

1. A system for detecting and locating sources of radiation emissions, comprising:
   a hand-held probe including:
      a detector configured to generate a low-level electrical signal relating to gamma data emitted by a radiation source proximate the detector;
      a preamplifier configured to amplify the low-level electrical signal to a corresponding output electrical signal representing the gamma data;
      a controller configured to receive the output electrical signal, convert the output electrical signal to gamma data, and generate messages containing a predetermined number of bytes relating to the gamma data, and transmit the messages; and
      a probe wireless link configured to receive the messages from the controller, periodically transmit the messages containing gamma data relating to the low-level electrical signal; and
   an instrumentation console including:
      a housing,
      a console wireless link within the housing and configured to receive the messages periodically transmitted by the probe wireless link,
      a receiver electrically coupled to the console wireless link to convert the received messages to corresponding electrical indication signals,
      an indicator to convert the electrical indication signals to a perceivable indication relating to the amount of radiation detected, and
      a signal processor coupled to the receiver, the signal processor configured to execute a smoothing function for processing the gamma data from the messages, wherein the smoothing function includes synchronizing the gamma count data into five millisecond time interval bins and averaging incoming gamma count data values over ten bins to derive a smoothed gamma count, and the console wireless link and the probe wireless link both being configured as transmitter-receivers for bidirectional communication of data.

2. The system of claim 1 wherein the probe wireless link and the console wireless link employ a radio frequency telecommunication protocol.

3. The system of claim 1 wherein the detector is a cadmium zinc telluride crystal.

4. The system of claim 1 wherein the detector is a cesium iodide scintillating device.

5. The system of claim 1 wherein the preamplifier is further configured to supply an electrical bias to the detector.

6. The system of claim 1, further comprising a universal asynchronous receiver/transmitter (UART) coupled to the console wireless link and to the receiver, the UART being configured to receive the message, convert the message to a serial data stream, and forward the serial data stream to the receiver.

7. The system of claim 1, wherein the indicator is an aural output configured to generate an aural signal relating to the gamma data.

8. The system of claim 1 wherein the console wireless link and the probe wireless link are both configured as at least one of radio frequency, visible light, infra-red light sonic and ultrasonic links.

9. The system of claim 1 wherein the indicator is a visually perceivable display electrically coupled to the receiver to convert the electrical signals to a visually perceivable indication relating to the amount of radiation detected.

10. The system of claim 1, wherein the hand-held probe further comprises:
a control switch in communication with the controller, the control switch being configured to allow adjustment of operating parameters relating to the gamma data generated by the probe, including at least one of a radiation target count and a calibration.

11. The system of claim 10, wherein the control switch is configured to allow adjustment of an operating parameter including a radiation target count.

12. The system of claim 1, wherein each of the messages comprises a start transmission character, a message type character, and the gamma data.

13. The system of claim 12, the gamma data being two bytes.

14. The system of claim 12, wherein each of the messages further comprises a checksum byte summing the other message bytes.

15. A system for detecting and locating sources of radiation emissions, comprising:
a hand-held probe including:
a cadmium zinc telluride detector crystal configured to generate a low-level electrical signal relating to gamma data emitted by a radiation source proximate the detector;
a preamplifier configured to amplify the low-level electrical signal to a corresponding output electrical signal representing the gamma data;
a controller configured to receive the output electrical signal, convert the output electrical signal to gamma data, and generate messages containing two bytes of information relating to the gamma data, and transmit the messages; and
an integral probe wireless link configured to receive the messages from the controller, periodically transmit the messages containing gamma data relating to the low-level electrical signal, the probe wireless link employing a radio frequency telecommunication protocol; and
an instrumentation console including:
a housing,
a console wireless link within the housing and configured to receive the message periodically transmitted by the probe wireless link, the console wireless link employing a radio frequency telecommunication protocol,
a receiver electrically coupled to the console wireless link to convert the messages to corresponding electrical display signals,
a visually perceivable display electrically coupled to the receiver to convert the electrical display signals to a visually perceivable indication relating to the amount of radiation detected, and
a signal processor coupled to the receiver, the signal processor configured to execute a smoothing function for processing the gamma data from the messages, wherein the smoothing function includes synchronizing the gamma count data into five millisecond time interval bins and averaging incoming gamma count data values over ten bins to derive a smoothed gamma count, and the console wireless link and the probe wireless link both being configured as transmitter-receivers for bidirectional communication of data.

16. The system of claim 15 wherein the instrumentation console further includes a signal processor electrically coupled to the receiver, the signal processor configured to be adjustable to establish a desired gamma data threshold to be displayed.

17. The system of claim 15, further comprising a universal asynchronous receiver/transmitter (UART) coupled to the console wireless link and to the receiver, the UART being configured to receive the message, convert the message to a serial data stream, and forward the serial data stream to the receiver.

18. The system of claim 15, wherein the hand-held probe further includes:
a control switch in communication with the controller, the control switch configured to allow adjustment of operating parameters relating to the gamma data generated by the probe, including at least one of a radiation target count, a time-interval accumulated count, and a calibration.

19. A method for detecting and locating sources of radiation emissions, comprising the steps of:
providing a hand-held probe having a detector, a preamplifier, a controller, a control switch in communication with the controller, and a probe wireless link configured to periodically transmit messages;
providing an instrumentation console having a housing, a console wireless link within the housing configured to receive the messages periodically transmitted by the probe wireless link, a receiver electrically coupled to the console wireless link, and a visually perceivable display electrically coupled to the receiver, the console wireless link and the probe wireless link are both configured as transmitter-receivers for bidirectional communication of data; and
placing the probe proximate a radiation source such that gamma radiation from the radiation source impinges upon the detector, the detector generating a low-level electrical signal relating to gamma data emitted by the radiation source, the preamplifier amplifying the low-level electrical signal to a corresponding output electrical signal representing the gamma data, the controller receiving the output electrical signal, converting the output electrical signal to gamma data, generating messages containing a predetermined number of bytes relating to the gamma data, and transmitting the messages to the probe wireless link, and
the probe wireless link receiving the messages from the controller, and periodically wirelessly transmitting the messages containing gamma data relating to the low-level electrical signal to the console wireless link, the receiver converting the messages to corresponding electrical display signal by executing a smoothing function, wherein the smoothing function includes synchronizing the gamma count data into five millisecond time interval bins and averaging incoming gamma count data values over ten bins to derive a smoothed gamma data count.

20. The method of claim 19, further comprising:
adjusting operating parameters relating to the gamma data generated by the probe using a control switch provided at the probe, the operating parameters including at least one of a radiation target count, a time-interval accumulated count, and a calibration.

* * * * *